United States Patent [19]
De Jonge et al.

[11] Patent Number: 5,170,049
[45] Date of Patent: Dec. 8, 1992

[54] COATING THICKNESS GAUGE USING LINEARLY POLARIZED LIGHT

[75] Inventors: Marinus W. C. De Jonge, Spierdijk; Tamis L. M. Leek, Alkmaar, both of Netherlands

[73] Assignee: Hoogovens Groep B.V., Ijmuiden, Netherlands

[21] Appl. No.: 441,641

[22] Filed: Nov. 27, 1989

[30] Foreign Application Priority Data

Nov. 28, 1988 [NL] Netherlands .................. 8802920

[51] Int. Cl.$^5$ .............................................. G02F 1/01
[52] U.S. Cl. .................... 250/225; 356/369
[58] Field of Search .............. 250/225, 559, 561, 571; 356/364, 365, 367, 369, 376, 381, 382

[56] References Cited

U.S. PATENT DOCUMENTS

| | | | |
|---|---|---|---|
| 3,426,201 | 2/1969 | Hilton et al. | 250/338.1 |
| 3,906,844 | 8/1975 | Hall | 250/225 |
| 3,908,508 | 8/1975 | Dubbeldam | 250/225 |
| 4,850,711 | 7/1989 | Sano et al. | 356/369 |

FOREIGN PATENT DOCUMENTS 0075689 4/1983 European Pat. Off. .
2618953 11/1976 Fed. Rep. of Germany .

OTHER PUBLICATIONS

A. Torao, "Method for Measuring Thickness of Surface Film" Patent Abstracts of Japan vol. 7 No. 109 (P-196) (1254) May. 1983.

M. Ishino, "Method for Analyzing Deflection of Thin Film" Patent Abstracts of Japan vol. 9 No. 157 (P-369) (1880) Jul. 1985.

Primary Examiner—David C. Nelms
Assistant Examiner—Stephone B. Allen
Attorney, Agent, or Firm—Stevens, Davis, Miller & Mosher

[57] ABSTRACT

A coating thickness gauge for measuring the thickness of a coating of chromic oxideon a chromium layer on a substrate has a light source 17 for generating linearly polarized light, means 19 for splitting elliptically polarized light reflected through the chromic oxide coating into a plurality of beams 20, 21, detectors 22, 23 for intensity of each of the beams and means 24 for calculating the thickness of the coating of chromic oxide from the measured intensities. To simplify the device and the calculation, the splitting means are arranged to split the reflected elliptically polarized light into two partial beam 20, 21 polarized at a known angle relative to each other and the calculation means calculate the ellipticity from the measured intensity of the two partial beams and the thickness from the ellipticity.

12 Claims, 1 Drawing Sheet

COATING THICKNESS GAUGE USING LINEARLY POLARIZED LIGHT

BACKGROUND OF THE INVENTION

1. Field of the Invention

The invention relates to a coating thickness gauge for measuring the thickness of a coating of chromic oxide on a chromium layer on a substrate using polarized light, and to a method of measuring the thickness of such a layer using the gauge.

2. Description of the Prior Art

A coating thickness gauge is known from EP-A-249235 which is based on the principles of ellipsometry. The gauge comprises a light source for generating linear polarized light, fixed splitting means for splitting elliptically polarized light reflected through the coating into a number of beams, a measuring apparatus for measuring the intensity of each of the beams and calculation means for calculating the thickness of the coating from the intensities measured.

In use of this gauge an incident beam of linear polarized light is directed onto a coating to be measured. The part of the incident beam with a direction of polarization parallel to the plane of incidence, that is the plane through the incident beam and the reflected, beam, is reflected differently both in phase and in amplitude from the part of the beam with a direction of polarization perpendicular to the plane of incidence. The result is a reflected beam which, in general, is elliptically polarized; that means that the electrical field strength in a plane perpendicular to the direction of the reflected beam describes an ellipse. The ratio $r_p/r_s$ between the complex amplitude reflection coefficients in the parallel direction and in the perpendicular direction is a measure for the thickness of the coating. This ratio is measured by making use of the relation $r_p/r_s = \tan \Psi \exp j \Delta$ and measuring $\Psi$ and $\Delta$ and one intensity. In this relation $\Psi$ is the azimuth angle and the angle $\Delta$ is calculated from the ratio between the long axis and the short axis of the ellipse, known as the ellipticity.

In the gauge of EP-A-249235 the measurement is made by dividing the reflected beam into at least three partial beams using semi-transparent mirrors as means of splitting. The partial beams are each monitored by an analyzer, each analyzer having a different angle of polarization. The intensity of the partial beam in each of the three directions of polarization is measured using a measuring apparatus suited to the purpose, such as a photodetector.

From the ratio of the three intensities in different directions of polarization and using the means of calculation, the azimuth angle $\Psi$ and the ellipticity of the ellipse may be calculated. From these, making use of the above relation the thickness of the reflecting coating may be obtained.

An inconvenience of this known apparatus is that the optical system needed is relatively complicated and puts great demands on optical alignment. This is a particular disadvantage in a production environment e.g. for coated steel sheet. Another inconvenience is that for a precise thickness measurement the optical properties of the components used must be known exactly. This inconvenience applies particularly to semi-transparent mirrors because semi-transparent mirrors affect the direction of polarization of both the transmitted and the reflected beams. This causes an error in determining the ellipse. Another inconvenience is that a great number of calculations have to be made for obtaining the thickness of the reflecting coating.

A thickness gauge provided with a polarizing beam splitter is known from EP-A-278577. This describes a coating thickness gauge for measuring the thickness of a coating of protein on a substrate. In the coating thickness gauge described the incident beam is thrown onto the coating of protein at the Brewster angle and by means of a polarizing beam splitter the reflected beam is split into a parallel partial beam $R_p$ and a perpendicular partial beam $R_s$.

Therefore, this coating thickness gauge only gives information about the azimuth angle $\Psi$ and is not suitable for measuring the thickness of a coating of chromic oxide.

Making use of the formula $M=(R_s-mR_p)/(R_s+mR_p)$ in accordance with the publication, M can be calculated an M is a measure for the coating thickness. The coating thickness gauge described is intended particularly for use when the incident and the reflected beams vary in intensity, for example as a result of an absorbing substrate through which the light must pass in order to reach the coating to be measured. The Brewster angle as angle of incidence in the coating thickness gauge described is only significant for substrates which have a true refractive index. In the case of a chromic oxide coating on chromium, a Brewster angle is not defined because chromium has a complex refractive index.

SUMMARY OF THE INVENTION

The object of the invention is to provide a simpler coating thickness gauge which is suitable in particular for measuring the thickness of a coating of chromic oxide on a chromium layer on a substrate.

Another object of the invention is to provide a coating thickness gauge which is particularly suitable for use in a production environment.

The present invention provides a coating thickness gauge for measuring the thickness of a coating of chromic oxide on a chromium layer on a substrate, comprising a light source for generating linearly polarized light and directing said light onto the chromic oxide coating, splitting means for splitting elliptically polarized light reflected through the chromic oxide coating into two partial beams polarized at a predetermined angle to each other, detection means for measuring the intensity of each of the partial beams and calculation means adapted and arranged for calculating the ellipticity of the reflected polarized light from the measured intensity of the two partial beams and for calculating the thickness of the coating from the ellipticity. The substrate can be steel, chromium or any other material.

Surprisingly it has been found from tests that, for normal coating thicknesses, when reflecting linearly polarized light from a coating of chromic oxide on chromium, within a certain range of constant incident angles of the linearly polarized light, the azimuth angle $\Psi$ of the reflected light and consequently the angle of the long axis of the ellipse are constant relative to the plane of incidence. The incident angle is the angle between the beam of linear polarized light and the normal to the substrate. With a constant and known azimuth angle $\Psi$, it is then entirely possible to determine the angle $\Delta$ by splitting the reflected beam into two partial beams polarized at a known angle relative to each other and to measure the intensity of each partial beam. From the two measured intensities the angle $\Delta$ can be calculated. The thickness of the coating to be measured can be determined directly form the then known ellipticity of the ellipse determined in that way.

EP-A-75689 describes a photometric polarimeter in which the reflected light beam from a sample is passed to a polarizing beam splitter. The split reflected beams go to detectors for respectively the perpendicular and parallel polarized portions of the beam. The detector outputs are used to obtain information about the specimen. Possible information obtained concerns film growth on the sample. From the perpendicular and parallel polarized portions of the beam, only the angle $\Psi$ can be calculated. In the case of chromic oxide on chrome it has been found that the angle $\Psi$ is practically constant. Therefore this apparatus is not suitable for use in determining chromic oxide layer thickness. When applied to layer thickness measurement, it involves also measurement of the incident beam intensity, for normalization, in order that the ellipticity of polarization of the reflected beam can be calculated. This means that three intensities are measured and used in the calculation.

Preferably said predetermined angle is 90° and in particular it is preferred that the splitting means are adapted for splitting the reflected beam into a partial beam polarized in the direction of the long axis and into a partial beam polarized in the direction of the short axis. In this particular case it is simple to calculate back to the ellipticity from the ratio between the intensities measured.

Particularly simple and particularly suitable for use in a production environment is a coating thickness gauge in accordance with the invention in which the splitting means comprise a "polarizing beam splitter". In accordance with the finding of the inventors, the azimuth angle $\Psi$ at which the ellipse stands is constant and known within a wide range of constant incident angles. With a known azimuth angle $\Psi$ the polarizing beam splitter may be positioned in such a way that the two partial beams emerging from it are the electrical field components along the two principal axes of the ellipse.

Thus according to the invention, the calculating means preferably has fixed data, relating to the known and constant azimuth angle $\Psi$, which is used in the calculation of the ellipticity from the measured intensities.

Preferably the coating thickness gauge in accordance with the invention has a compensator for displacing together in phase the two beams polarized at a known angle to each other. This embodiment is particularly suitable for measuring the coating thickness in those cases where the angle $\Delta$ is in the region of 90°.

In practice good results are obtained with a coating thickness gauge in accordance with the invention in which the light source is set up so that the linear polarized light meets the substrate at an angle of approx. 60° to the normal line to the substrate surface. Within certain limits the sensitivity of the coating thickness gauge increases with increase of the angle between the incident beam and the normal to the substrate, i.e. the incident angle. It has been found that the angle $\Psi$ is constant over a considerable range of the incident angle. Over a range from 0° to approx. 70° $\Psi$ varies very little and is about 40°. However, the sensitivity of $\Delta$ for the thickness of the coating varies with the incident angle and has been found to have a practical optimum at an incident angle of approx. 60°. An inconvenience of a large angle is that the light source and the splitting means must be set up close to the plane of the substrate. If the substrate is a moving strip, then the light source and the splitting means are vulnerable. A good compromise between vulnerability, operational reliability and sensitivity is found at an angle of approx. 60°, e.g. 50 to 70. For practical purposes of measuring the thickness of a chromic oxide layer on chrome the angle is constant within this range.

The sensitivity of the coating thickness gauge is good when the light source is suitable for transmitting a light with a wavelength of between 633 and 254 nm. It is preferable to select the smallest possible wavelength which it is practical to achieve because with smaller wavelengths the sensitivity of the coating thickness gauge increases.

The accuracy of the coating thickness gauge may be further increased if it is provided with support means for maintaining the angle of incidence of the incident light constant and in particular if the support means comprises a carrier roller for supporting the light source on the substrate, e.g. a roller directly contacting a moving substrate. The sensitivity of the coating thickness gauge depends on the angle of incidence between the incident beam and the normal to the substrate. As a result of this the thickness measured also depends on variations in the angle of incidence. With a support of the light source, the position of the substrate relative to the incident beam light is completely fixed and so too is the angle of incidence.

A coating of chromic oxide as discussed here not limited to a coating of pure chromic oxide, but also includes a coating essentially containing chromic oxide as occurs on chromed steel. Such a chromic oxide coating also contains chromic hydroxide, impurities and pores.

In practice it is found that the accuracy of the coating thickness gauge for such a chromium layer is increased if the gauge is provided with adjustment means for adjusting the calculated thickness to an absolutely specific quantity of chromic oxide per unit of surface area of a substrate. Using an absolute chemical measuring method such as AAS/photometry the quantity of chromium in the coating of the chromic oxide per unit of surface area is measured. From the result obtained in this way, the coating thickness may be calculated, and using the adjustment means the value calculated by the coating thickness gauge is made to correspond with it.

An embodiment of the invention will now be illustrated by way of non-limitative example with reference to the drawing.

DESCRIPTION OF THE PREFERRED EMBODIMENT

Figure 1:
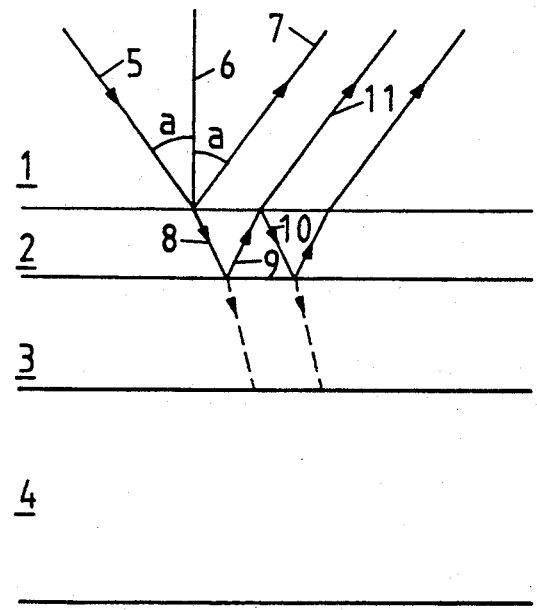
Figure 2:
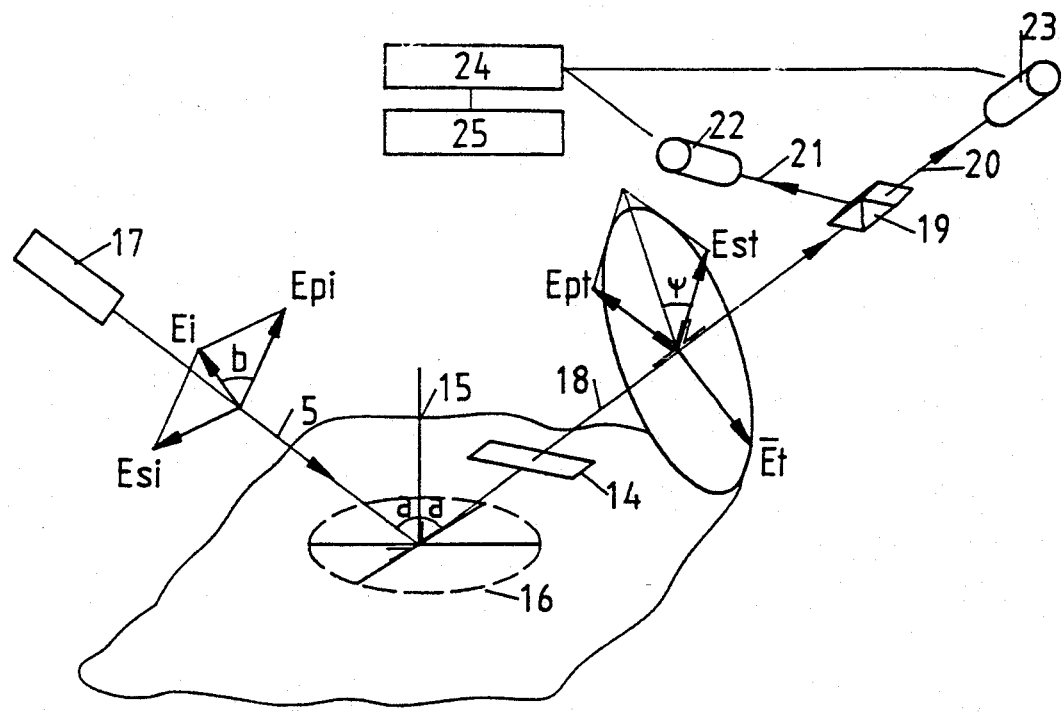

FIG. 1 gives a schematic representation of the reflection of a light beam on a thin coating, and FIG. 2 gives a schematic representation of a coating thickness gauge in accordance with the invention.

FIG. 1 shows a cross-section through a chromed steel sheet. The figure shows the air 1 above the sheet, a coating 2 of chromic oxide of which the thickness is to be measured, a layer 3 of chromium, and a substrate 4 of steel. During the electrolytic chroming of steel strip a coating of chromium deposits onto the steel, but on the layer of chromium at the side facing away from the steel is formed a coating essentially of chromic oxide, but also containing chromic hydroxide, impurities and pores. In this description the coating of chromic oxide coating as well as one as formed in practice.

A beam of light falls onto the surface of the chromed steel sheet at an angle a to the normal line 6 to the substrate. A part of this beam is reflected at the same angle a as beam 7. A part of the beam 6 is refracted at the transition 1 - 2 and penetrates the chromic oxide coating 5 as a reflected beam 8. A part of the refracted beam 8 is reflected at the transition 2 - 3 and returns to the transition 1 - 2 as beam 9. In its turn, beam 9 is again partially reflected to the transition 1 - 2 as beam 10 and partially leaves the coating of chromic oxide as beam 11. Together, all the beams coming off the chromic oxide surface in accordance with the process described here form the reflected beam.

FIG. 2 shows the incident beam 5 which forms an incident angle a to the normal line 15 to the surface of the chromed strip 16. The beam 5 is generated by means of helium-neon laser 17. Vector Ei indicates the direction of polarization of the incident beam. Vector Ei is resolved into a component Epi and a component Esi. Component Epi is parallel to the plane of incidence through the incident beam 5 and the reflected beam 18; the component Esi is perpendicular to the plane of incidence.

The direction parallel to the plane of incidence is called the p-direction; the direction perpendicular to the plane of incidence is called the s-direction. It is generally preferable to select the angle b between vector Ei and its component Epi to be 45° so that Epi and Esi are equal in size. The beam 18 reflected through the coating of chromic oxide on the chromed strip 16 is elliptically polarized. The end of the electrical field vector Et of the reflected light describes an ellipse in a plane perpendicular to the reflected beam.

The electrical field vector Et has an amplitude in the p-direction indicated by Ept, and an amplitude in the s-direction indicated by Est.

The relation $Ept/Est = r_s = \tan \Psi \exp j \Delta$ now applies. The thickness of the coating of chromic oxide 2 which has caused the reflected beam, may be derived from the ellipsometric magnitudes $\Psi$ and $\Delta$. Surprisingly it is found that for the chromium/chromic oxide combination the azimuth angle $\Psi$ is more or less constant and approximately 40°, independent of the thickness of the chromic oxide coating, and that only the ellipticity, that is the ratio between the short and the long axis, of the ellipse varies with the thickness of the coating of chromic oxide. Because the azimuth angle $\Psi$ is constant and about 40°, the ellipse angle formed by the long axis of the ellipse to the s-direction is also constant and approximately 40°.

Therefore, depending on the chosen mechanical set up of the thickness gauge, it is possible to choose the polarization of the beam 5 such that the azimuth angle $\Psi$ is constant at an angle of 45°.

The ratio of the short axis and the long axis is determined by letting the reflected beam fall onto a polarizing beam splitter 19 positioned at the ellipse angle of approx. 45°. When measuring a coating whose angle $\Delta$ lies in the region of $\pi/2$ radians, the short axis is comparatively long. In order to maintain the sensitivity of the coating thickness gauge, the coating thickness gauge is provided with a compensator 14 which alters the angle $\Delta$ by a set amount. The intensity of each of the two beams 20 and 21 emerging from the polarizing beam splitter is measured using photodetectors 22 and 23.

The output of each of the photodetectors 22 and 23 is linked to a calculating unit 24. The calculating unit calculates the ratio q of the long axis of the ellipse and the short axis of the ellipse by extracting the root of the quotient of the two intensities measured. Within some practical limits, this ratio q is related according to a linear relation $q = A - Bd$ to the thickness d of the coating of chromic oxide. The constants A and B are determined by means of an absolute measuring method. AAS/photometry is found to be a suitable absolute method.

Because the calculating unit 24 already in effect contains fixed data relating to the constant azimuth angle $\Psi$ for reflection from a chromic oxide layer, $\Psi$ does not need to be separately measured, and it is possible to calculate the ellipticity of polarization only from the outputs of the two detectors 22, 23. Measurement of the incident beam intensity is not needed. Thus the measurement and the calculation are both simple.

The thickness measuring apparatus is particularly suitable for continuously measuring the chromic oxide coating and as a measuring unit in an automated system. An X-ray fluorescence apparatus may be used for the total chromium quantity on the steel strip. In practice the thickness of the layer of chromium is approx. 10 nm and the thickness of the coating of chromic oxide between 2 and 4 nm.

What is claimed is:

1. Coating thickness gauge for measuring the thickness of a coating of chromic oxide on a chromium layer on a substrate, comprising a light source for generating linearly polarized light and directing said light onto the chromic oxide coating, splitting means for splitting elliptically polarized light reflected through the chromic oxide coating into two partial beams polarized at a predetermined angle to each other, detection means for measuring the intensity of each of the partial beams and calculation means adapted and arranged for calculating the ellipticity of the reflected polarized light from the measured intensity of the two partial beams and for calculating the thickness of the coating from the ellipticity.

2. Coating thickness gauge in accordance with claim 1, wherein said predetermined angle is 90°.

3. Coating thickness gauge in accordance with claim 2, wherein said splitting means are adapted to split the reflected light into a first said partial beam polarized in the direction of the long axis and into a second said partial beam polarized in the direction of the short axis of the polarization ellipse.

4. Coating thickness gauge in according to claim 1 wherein said calculating means has fixed data relating to the constant azimuth angle $\Psi$ of the elliptically polarized light, which data is used in the calculation of the ellipticity from the measured intensities of the partial beams.

5. Coating thickness gauge in accordance with claim 1 wherein the splitting means comprise a polarizing beam splitter.

6. Coating thickness gauge in accordance with claim 1 provided with a compensator for moving together in phase the two partial beams polarized at a predetermined angle to each other.

7. Coating thickness gauge in accordance with claim 1 wherein the light source is arranged so that the linearly polarized light meets the substrate at an angle of about 60° to the normal to the substrate surface.

8. Coating thickness gauge in accordance with claim 1 wherein the light source is adapted to transmit light with a wavelength of between 633 and 254 nm.

9. Coating thickness gauge in accordance with claim 1 provided with support means for maintaining constant the angle of incidence of the incident light on the substrate surface.

10. Coating thickness gauge in accordance with claim 9, wherein said support means comprise a carrier roller for supporting the light source on the substrate.

11. Coating thickness gauge in accordance with claim 1 provided with adjustment means for adjusting the calculated thickness to an absolutely specific quantity of chromic oxide per unit of surface area of the substrate.

12. Method of measuring thickness of a chromic oxide layer wherein a gauge in accordance with claim 1 is used.

* * * * *